(12) United States Patent
Stopp et al.

(10) Patent No.: US 12,390,289 B2
(45) Date of Patent: Aug. 19, 2025

(54) ROBOTIC MANIPULATION OF MEDICAL CARRIER STRUCTURES

(71) Applicant: Brainlab AG, Munich (DE)

(72) Inventors: Sebastian Stopp, Munich (DE); Nils Frielinghaus, Munich (DE)

(73) Assignee: Brainlab AG, Munich (DE)

( * ) Notice: Subject to any disclaimer, the term of this patent is extended or adjusted under 35 U.S.C. 154(b) by 308 days.

(21) Appl. No.: 18/009,547

(22) PCT Filed: Jul. 6, 2020

(86) PCT No.: PCT/EP2020/069018
§ 371 (c)(1),
(2) Date: Dec. 9, 2022

(87) PCT Pub. No.: WO2022/008034
PCT Pub. Date: Jan. 13, 2022

(65) Prior Publication Data
US 2023/0225805 A1 Jul. 20, 2023

(51) Int. Cl.
*A61B 34/30* (2016.01)
*A61B 90/50* (2016.01)

(52) U.S. Cl.
CPC .............. *A61B 34/30* (2016.02); *A61B 90/50* (2016.02); *A61B 2090/508* (2016.02)

(58) Field of Classification Search
None
See application file for complete search history.

(56) References Cited

U.S. PATENT DOCUMENTS

| | | | | |
|---|---|---|---|---|
| 6,645,196 | B1* | 11/2003 | Nixon | A61B 34/37 606/1 |
| 2010/0332032 | A1* | 12/2010 | Moriyama | B25J 9/1633 700/258 |
| 2012/0130399 | A1* | 5/2012 | Moll | G16H 40/63 606/130 |
| 2018/0147105 | A1 | 5/2018 | Timm et al. | |
| 2022/0000571 | A1* | 1/2022 | Griffiths | A61B 34/10 |

FOREIGN PATENT DOCUMENTS

| WO | 2020020749 A1 | 1/2020 |
|---|---|---|
| WO | 2020092775 A1 | 5/2020 |
| WO | 2000030548 A1 | 6/2020 |

OTHER PUBLICATIONS

International Search Report dated Mar. 24, 2021 for Application Serial No. PCT/EP2020/069018, 3 pages.
Written Opinion of the International Searching Authority dated Mar. 24, 2021 for Application Serial No. PCT/EP2020/069018, 11 pages.

\* cited by examiner

*Primary Examiner* — Adam R Mott
*Assistant Examiner* — Alan Lindsay Ostrow
(74) *Attorney, Agent, or Firm* — Tucker Ellis LLP (57) ABSTRACT

The present disclosure relates to a system and a computer-implemented medical method for manipulating at least one first, non-motorized medical carrier structure via a second, motorised medical carrier structure, wherein the second, motorized medical carrier structure is adapted to engage the first, non-motorized carrier structure to subsequently move a predefined section of the non-motorized carrier structure to a desired target position. The present disclosure further relates to a corresponding computer program and a corresponding medical system.

16 Claims, 4 Drawing Sheets

ROBOTIC MANIPULATION OF MEDICAL CARRIER STRUCTURES

RELATED APPLICATION DATA

This application is a National Phase application of International Application No. PCT/EP2020/069018, filed Jul. 6, 2020, the contents of which are incorporated herein by reference.

FIELD OF THE INVENTION

The present invention relates to a computer-implemented method and system for manipulating at least one first, unmotorised medical carrier structure via a second, motorised medical carrier structure, a corresponding computer program, a computer-readable storage medium storing such a program and a computer executing the program, as well as a medical system comprising an electronic data storage device and the aforementioned computer.

TECHNICAL BACKGROUND

In recent years, surgical procedures have seen an increased use of robotic systems which not only help doctors to perform complex operations on a patient, but also allow such procedures to be performed with a persisting and also higher precision than it would be possible with conventional/manual techniques.

Such robotic systems include carrier structures which may specifically take the shape of an articulated support arm and which may be subclassified in passive systems and active systems. While the main use of passive systems is to hold medical devices, medical appliances and similar in a desired spatial position (spatial location and/or spatial orientation) and need to be aligned manually by a user, active systems feature actuators/motors and can therefore align autonomously and may even move medical devices, medical appliances or similar which they are currently holding. In order to align autonomously, such active carrier structures may comprise position encoders that deliver data on which basis the current spatial configuration of the carrier structure can be calculated, and therefore do not necessarily have to be tracked by an external tracking system as it is often the case with passive carrier structures without position encoders. On the other hand, utilising an expensive active carrier structure for just holding instruments or appliances in place for a long period of time is not considered cost-efficient.

The present invention has the object of providing a method and a system which benefits from advantages of both, unmotorised and motorised carrier structures, The present invention can be used for robot assisted surgical procedures e.g. in connection with a system such as Cirq®, a product of Brainlab AG.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

The present invention relates to a system and a computer-implemented medical method for manipulating at least one first, unmotorised medical carrier structure via a second, motorised medical carrier structure, wherein the second, motorised medical carrier structure is adapted to engage the first, unmotorised carrier structure to subsequently move a predefined section of the unmotorised carrier structure to a desired target position. The present invention further relates to a corresponding computer program and a corresponding medical system.

GENERAL DESCRIPTION OF THE INVENTION

In this section, a description of the general features of the present invention is given by referring to possible embodiments of the invention.

The present invention reaches the aforementioned object by providing, in a first aspect, a computer-implemented medical method of manipulating at least one first, unmotorised medical carrier structure via a second, motorised medical carrier structure, wherein the at least one first carrier structure comprises at least one first adjustable and selectively fixable joint which respectively connects two sections of the first carrier structure, and in particular comprises at least one first mechanical interface at one or more of the sections and/or at one or more of the fixable joints, specifically at a first predefined section, and wherein the second carrier structure comprises a second mechanical interface and at least one second adjustable and in particular selectively fixable joint which respectively connects two sections of the second carrier structure, the method comprising the following steps:

- interface data is acquired which describes the spatial position of a section or a joint of the first carrier structure, particularly of a first mechanical interface, to be engaged by the second mechanical interface;
- engage data is determined based on the interface data, which describes control information to cause the second carrier structure to move the second mechanical interface to a spatial position in which the second mechanical interface engages with the section or joint of the first carrier structure, particularly the first mechanical interface;
- target position data is acquired which describes a target position for a first predefined section of the first carrier structure;
- positioning data is determined based on the target position data, which describes control information to cause the second carrier structure to move the first predefined section to the target position.

The method comprises executing, on at least one processor of at least one computer (for example at least one computer being part of a navigation system), the following exemplary steps which are executed by the at least one processor.

In a (for example first) exemplary step, data is acquired that describes at which spatial position a mechanical interface of the motorised carrier structure shall engage the unmotorised carrier structure. In general, this can be any part of the unmotorised carrier structure which is suited to establish a solid mechanical connection with the mechanical interface of the motorised carrier structure for being moved, along with the first predefined section of the unmotorised carrier structure, to a desired spatial position. Moreover, the term "mechanical interface" can include any active or passive structure that is able to provide a mechanically stable, force transmitting connection between the carrier structures. Such engagement section can be for example at any section or joint of the unmotorised carrier structure, as long as it can be connected invariantly to the first predefined section until the latter has reached its target position. It is conceivable that the unmotorised carrier structure does not feature specifically designed sections for a mechanical interface to engage at. Provided that the mechanical interface of the motorised carrier structure is adapted to grip arbitrarily formed objects, a conventional, unmotorised carrier structure "can stay as it is" and does not need to be modified to enable a connection with the mechanical interface of the motorised carrier structure. On the other hand, any one or a plurality of the sections and/or joints of the unmotorised carrier structure may comprise a specifically designed engagement section adapted to be gripped by the mechanical interface of the motorised carrier structure. For example, such section may be formed as a passive handle or may be formed as an active mechanical interface which corresponds or even may substitute an active mechanical interface of the motorised carrier structure that may then be formed as a passive handle.

More specifically, any designated mechanical interface of the motorised carrier structure as well as of the unmotorised carrier structure may be formed by:
- an active electro-mechanical interface which may for example comprise active driven clamps or spring-based interlocks, adapted to establish a releasable friction-fit or form-fit with corresponding parts of the respective other carrier structure;
- a magnetic connection which may for example comprise one or more electromagnets to establish a releasable connection with corresponding ferromagnetic parts of the respective other carrier structure;
- a connection which is uphold by gravity, wherein the unmotorised carrier structure may "rest" on the motorised carrier structure, for example via correspondingly formed surfaces, wherein the surface of the unmotorised carrier structure is held on the corresponding surface of the motorised carrier structure by gravity. In a specific example, the mechanical interface of the motorised carrier structure may comprise a recess which opens in an upward direction, into which a correspondingly formed protrusion of the unmotorised carrier structure may enter in a downward direction.

While it is conceivable that the mechanical interface leaves no degree of freedom for the gripped carrier structure, other embodiments of the mechanical interface may allow for one or more rotational and/or translational degree(s) of freedom. For example, the mechanical interface may comprise jaws having a concave surface in at least one dimension, which may releasably engage a handle having a convex surface in at least one dimension, thereby leaving one or more rotational degrees of freedom for the gripped carrier structure.

For acquiring the interface data, the engagement section of the unmotorised carrier structure may be tracked by a medical tracking system. For example, an external tracking system may recognise one or more (optical) tracking markers which indicate the spatial position of the engagement section. Moreover, the engagement section's spatial position may also be derived based on data acquired from position sensors/encoders at the joints of the unmotorised carrier structure, from which the spatial configuration of the unmotorised carrier structure can be calculated. The expression "spatial configuration" as used herein is to define the relative positions of the carrier structure's sections with respect to each other. Once the absolute spatial position of one of the sections is known, the absolute spatial position of every other section can be calculated from a model that describes the spatial configuration of the carrier structure.

The spatial position of the engagement section may however also be determined based on near field communication (NFC) technology. For example, the engagement section may feature an RFID-transponder which can be identified by the motorised carrier structure's mechanical interface so as to approach the correct position for engaging with the engagement section.

Further, the engagement section's spatial position may be shown in an augmented reality (AR)-environment provided to a user with the help of semi-transparent AR-spectacles, AR-googles or similar visualisation devices.

In a (for example second) exemplary step, engage data is calculated based on the interface data, which describes to which spatial position the mechanical interface of the motorised carrier structure needs to be moved in order for it to engage the unmotorised carrier structure.

This can be done by a control unit, which may receive data which describes the spatial configurations of both carrier structures, or at least the relative spatial position between the mechanical interface and the engagement section. Based on this data, the control unit may be adapted to control the motors/actuators as well as an active mechanical interface of the motorised carrier structure to approach and respectively engage the unmotorised carrier structure. For receiving, issuing and/or transmitting data, the control unit may be connected with a respective carrier structure via a wired or a wireless connection.

In a (for example third) exemplary step, target position data is acquired which describes a desired spatial position in which a predefined section of the unmotorised carrier structure is to be positioned to fulfil its purpose, for example for holding a medical instrument at a desired spatial location with a desired spatial orientation.

Based on the acquired target position data, positioning data is calculated which describes the necessary movement of the motorised carrier structure to position the predefined section of the unmotorised carrier arm in its desired target position.

As the mechanical interface of the motorised carrier structure does not necessarily engage an unmotorised carrier structure at its predefined section, but may rather engage any other suitable part of the unmotorised carrier structure, calculating the positioning data may further consider the current spatial configuration of the unmotorised carrier structure, which may not only include the relative position of the sections with respect to each other, but also the range of motion which is currently provided by the respective joints of the unmotorised carrier structure. With the current spatial configuration of the unmotorised carrier structure known, it is not only possible to calculate the spatial position to which the engagement section needs to be moved in order for the predefined section of the unmotorised carrier structure to reach its target position, but also which engagement section of a possible plurality of engagement sections of the unmotorised carrier structure is best engaged by the mechanical interface for moving the predefined section to its target position. It is generally conceivable that, if the predefined section of the unmotorised carrier structure cannot be positioned at once in its desired target position with the current alignment of the joints of the unmotorised carrier structure, the mechanical interface engages and moves a plurality of engagement sections in sequence to eventually position the predefined section at the desired target position.

In a more specific example of the method according to first aspect, the at least one first joint of the unmotorised carrier structure comprises a controllable first locking mechanism, for example a locking brake, wherein
the engage data includes control information to release the first locking mechanism after the second mechanical interface has engaged with the first carrier structure and/or before the second carrier structure moves the first predefined section to the target position; and/or the positioning data includes control information to lock the first locking mechanism after the second carrier structure has moved the first predefined section to the target position.

In other words, the locking brakes of the unmotorised carrier structure are released as soon as the mechanical interface of the motorised carrier structure has engaged the unmotorised carrier structure, wherein the brakes are locked again as soon as the predefined section of the unmotorised carrier structure has reached its desired position and the mechanical interface may therefore release the unmotorised carrier structure again. The signals for locking and releasing the locking brakes may be issued by the control unit.

In a further specific example of the inventive method, the mechanical interface of the motorised carrier structure and/or the mechanical interface of the unmotorised carrier structure comprises a controllable/releasable engaging mechanism, wherein the engage data includes control information to cause the engaging mechanism to establish a force transmitting connection between the first and the second carrier structure after the second mechanical interface has engaged with the first carrier structure; and/or the positioning data includes control information to cause the engaging mechanism to release the force transmitting connection between the first and the second carrier structure after the first locking mechanism has locked.

In other words, the engaging mechanism is activated to engage the unmotorised carrier structure as soon as the mechanical interface of the motorised carrier structure has reached its respective position, wherein the engaging mechanism is released again after the predefined section of the unmotorised carrier structure has reached its desired position and the locking brakes of the unmotorised carrier structure's joints have been locked. The corresponding signals to the engagement mechanism can be again issued by the control unit.

Just like the unmotorised carrier structure, the motorised carrier structure may also comprise controllable locking mechanisms or brakes for locking its joints. The positioning data may then include control information to lock the locking mechanism of the motorised carrier structure after it has moved the predefined section of the unmotorised carrier structure to its target position. With the locking mechanisms being locked for both, the unmotorised carrier structure and the motorised carrier structure, and with the carrier structures still being rigidly connected via at least one mechanical interface, the carrier structures provide a most rigid and, compared with heavy-duty robots that need to be supported on a separate cart, comparatively light weight support structure which can sustain large loads applied via, for example, an instrument held by the unmotorised carrier structure.

In a further alternative example, the inventive method may comprise the steps of:

secondary target position data is acquired which describes a target position for a second predefined section of the second carrier structure;

secondary positioning data is determined based on the secondary target position data, which describes control information to cause the second carrier structure to move the second predefined section to the secondary target position.

Rather than remaining rigidly connected to each other, the unmotorised carrier structure may remain at its desired target position, while the motorised carrier structure may be released therefrom to approach another spatial position, for example to hold a medical device at separate spatial location. In general, the motorised carrier structure may proceed with any desired procedure, whilst the unmotorised carrier structure remains stationary at its desired position.

The first aspect of the present invention also includes a medical carrier system comprising:

at least one first, unmotorised medical carrier structure comprising at least one first adjustable and selectively fixable joint which respectively connects two sections of the first carrier structure, and in particular comprises at least one first mechanical interface at one or more of the sections and/or at one or more of the fixable joints, specifically at a first predefined section;

a second, motorised medical carrier structure comprising a second mechanical interface and at least one second adjustable and in particular selectively fixable joint which respectively connects two sections of the second carrier structure, wherein the second carrier structure is controlled by a control unit performing the method-steps as described above, to move the second mechanical interface to a spatial position in which the second mechanical interface engages with the unmotorised medical carrier structure, particularly the first mechanical interface thereof, and to move the first predefined section to a target position.

Such medical carrier system may of course comprise any one of the features described above in any meaningful combination.

More specific embodiments of such medical carrier system may be configured according to at least one of the following points:

the first carrier structure comprises a plurality of first joints, wherein each one of the first joints respectively connects two sections of the first carrier structure; and/or the second carrier structure comprises a plurality of second joints, wherein each one of the second joints respectively connects two sections of the second carrier structure; and/or at least one first joint and/or at least one second joint is a pivot joint providing a, particularly one rotational degree of freedom; and/or at least one first joint and/or at least one second joint comprises a position sensor adapted for determining the relative position of the sections connected via the respective joint; and/or the first predefined section is an end section of the first carrier structure and/or the second predefined section is an end section of the second carrier structure; and/or the first carrier structure comprises a spatially invariant first base section which connects to the first predefined section via the at least one first joint, and particularly via at least one first intermediate section; and/or the second carrier structure comprises a spatially invariant second base section which connects to the second predefined section via the at least one second joint, and particularly via at least one second intermediate section.

In a particular example, the motorised carrier structure and/or the unmotorised carrier structure may be represented by an articulated support arm which has a plurality of sequentially arranged arm sections connected to each other via rotatable joints. A first end section of a carrier structure may be a base section that takes a basically invariant spatial position. In this regard, spatially invariant means that the base section maintains its position within an operating theatre for at least a predefined period of time. For example, the base section may be disposed on a mobile cart or a similar appliance which maintains its spatial position within the operating theatre while a surgical procedure is carried out. In another example, the base section may be fixedly mounted to the floor or to the ceiling of the operating theatre. Further, spatially invariant may also mean that the base section maintains its spatial position with respect to the patient on which the surgical procedure is carried out. For example, the base section may be fixedly attached to the mounting rail of a patient couch. In a still further example, the base section takes an invariant position by remaining stationary within a reference coordinate system in which the spatial position of the patient and medical appliances including further sections of the carrier structure is calculated.

At the other end of the motorised carrier structure and/or the unmotorised carrier structure, which is opposite to the base section, the carrier structure may comprise an end section which includes or which fixedly connects to functional components such as an effector for holding or guiding medical instruments or devices with respect to the patient's anatomy.

According to a further specific example of the medical carrier system according to the first aspect of the invention, the first medical carrier structure comprises at least one first control interface, and the second medical carrier structure comprises at least one second control interface, wherein at least one first control interface and at least one second control interface are adapted to transmit, particularly via a wireless connection, control information between at least two of:
    the first, unmotorised medical carrier structure;
    the second, motorised medical carrier structure;
    a common control unit adapted to control the first medical carrier structure and/or the second medical carrier structure, particularly wherein one of the first and the second medical carrier structure is controlled via the control interface of the respective other medical carrier structure.

For example, a common control unit which is adapted to control the carrier structures, for example the actuators and/or brakes thereof, can be included by one of the carrier structures, but may also be provided as a component separate to the carrier structures.

In a further example, a first control interface is disposed at the first mechanical interface and a second control interface is disposed at the second mechanical interface, wherein the first control interface and the second control interface are adapted to transmit control information between the first and the second medical carrier structure when the second mechanical interface engages the first carrier structure.

With the control interfaces disposed like this, data can be transmitted between the carrier structures as soon as the mechanical interface of the motorised carrier structure has engaged the unmotorised carrier structure. In the alternative, it is of course also conceivable to control both of the carrier structures via independent data connections, i.e. via wireless or wire-based connections between the respective carrier structures and the control unit.

In a further example, the mechanical interface of the motorised carrier structure and/or of the unmotorised carrier structure is constituted by a holding and/or grasping section, which is in particular adapted to hold and/or grasp a medical instrument or device. Such holding and/or grasping sections are commonly known as effectors. Thus, the present invention can be implemented by utilising the existing effectors of at least one of the carrier structures without the need to provide a separate, designated mechanical interface. For example, the effector of the motorised carrier structure can be used to engage the unmotorised carrier structure, for example via a suitable and previously picked up adaptor, and, after being released from the unmotorised carrier structure to perform further tasks, lay down the engaging adaptor and pick up an instrument or other medical appliance directly or indirectly via another suitable adaptor.

In a further example, the mechanical interface of the motorised carrier structure and/or the unmotorised carrier structure, comprises at least one of:
    a controllable engaging mechanism adapted to establish and revoke a force transmitting connection between the first carrier structure, particularly the first mechanical interface and the second mechanical interface, particularly a releasable positive fit;
    a positioning aid configured to assist in positioning the second mechanical interface at a spatial position in which the second mechanical interface engages with the first carrier structure, particularly the first mechanical interface, specifically a magnetic and/or a physical positioning aid.

Moreover, any of the carrier structures can be adapted to output a signal that indicates whether a force transmitting connection between the unmotorised carrier structure, particularly the mechanical interface thereof, and the mechanical interface of the motorised carrier structure has been established and/or released. For example, a release and/or a locking state of a mechanical interface can be indicated to the user via a display, for example an AR-display as described above. Moreover, a warning signal could be output in case the force transmitting connection cannot be established and/or released.

Further, the mechanical interface of the motorised carrier structure and/or of the unmotorised carrier structure can be adapted to receive a load that is significantly higher than the load applied to the interfaces by moving the unmotorised carrier structure via the motorised carrier structure. Such "heavy duty" interfaces are particularly useful in case large loads are expected to be applied to the carrier structures via an instrument or other medical devices supported by the one or both of the carrier structures.

In a second aspect, the invention is directed to a computer program comprising instructions which, when the program is executed by at least one computer, causes the at least one computer to carry out method according to the first aspect. The invention may alternatively or additionally relate to a physical carrier carrying information which represents the program, for example the aforementioned program, which for example comprises code means which are adapted to perform any or all of the steps of the method according to the first aspect. A computer program stored on a disc is a data file, and when the file is read out and transmitted it becomes a data stream for example in the form of a (physical, for example electrical, for example technically generated) signal.

In a third aspect, the invention is directed to a computer-readable storage medium on which the program according to the second aspect is stored. The program storage medium is for example non-transitory.

In a fourth aspect, the invention is directed to at least one computer (for example, a computer), comprising at least one processor (for example, a processor), wherein the program according to the second aspect is executed by the processor, or wherein the at least one computer comprises the computer-readable storage medium according to the third aspect.

In a fifth aspect, the invention is directed to a medical system, comprising:
a) the at least one computer according to the fourth aspect;
b) at least one electronic data storage device storing at least the target position data; and
c) a medical carrier system according to the first aspect, wherein the at least one computer is operably coupled to the at least one electronic data storage device for acquiring, from the at least one data storage device, at least the target position data, and the medical carrier system for issuing a control signal to the medical carrier system for controlling the operation of the medical carrier system on the basis of the target position data.

Alternatively or additionally, the invention according to the fifth aspect is directed to a for example non-transitory computer-readable program storage medium storing a program for causing the computer according to the fourth aspect to execute the data processing steps of the method according to the first aspect.

Definitions

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term computer includes a server resource. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a computer program comprising instructions which, when on the program is executed by a computer, cause the computer to carry out the method or methods, for example, the steps of the method or methods, described herein and/or to a computer-readable storage medium (for example, a non-transitory computer-readable storage medium) on which the program is stored and/or to a computer comprising said program storage medium which represents the program, for example the aforementioned program, which for example comprises code means which are adapted to perform any or all of the method steps described herein. The invention also relates to a computer comprising at least one processor and/or the aforementioned computer-readable storage medium and for example a memory, wherein the program is executed by the processor.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows determining the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

The invention also relates to a navigation system for computer-assisted surgery, comprising:
a computer for processing the absolute point data and the relative point data;
a detection device for detecting the position of the main and auxiliary points in order to generate the absolute point data and to supply the absolute point data to the computer;
a data interface for receiving the relative point data and for supplying the relative point data to the computer; and
a user interface for receiving data from the computer in order to provide information to the user, wherein the received data are generated by the computer on the basis of the results of the processing performed by the computer.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

A fixed position, which is also referred to as fixed relative position, in this document means that two objects which are in a fixed position have a relative position which does not change unless this change is explicitly and intentionally initiated. A fixed position is in particular given if a force or torque above a predetermined threshold has to be applied in order to change the position. This threshold might be 10 N or 10 Nm. In particular, the position of a sensor device remains fixed relative to a target while the target is registered or two targets are moved relative to each other. A fixed position can for example be achieved by rigidly attaching one object to another. The spatial location, which is a part of the position, can in particular be described just by a distance (between two objects) or just by the direction of a vector (which links two objects). The alignment, which is another part of the position, can in particular be described by just the relative angle of orientation (between the two objects).

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
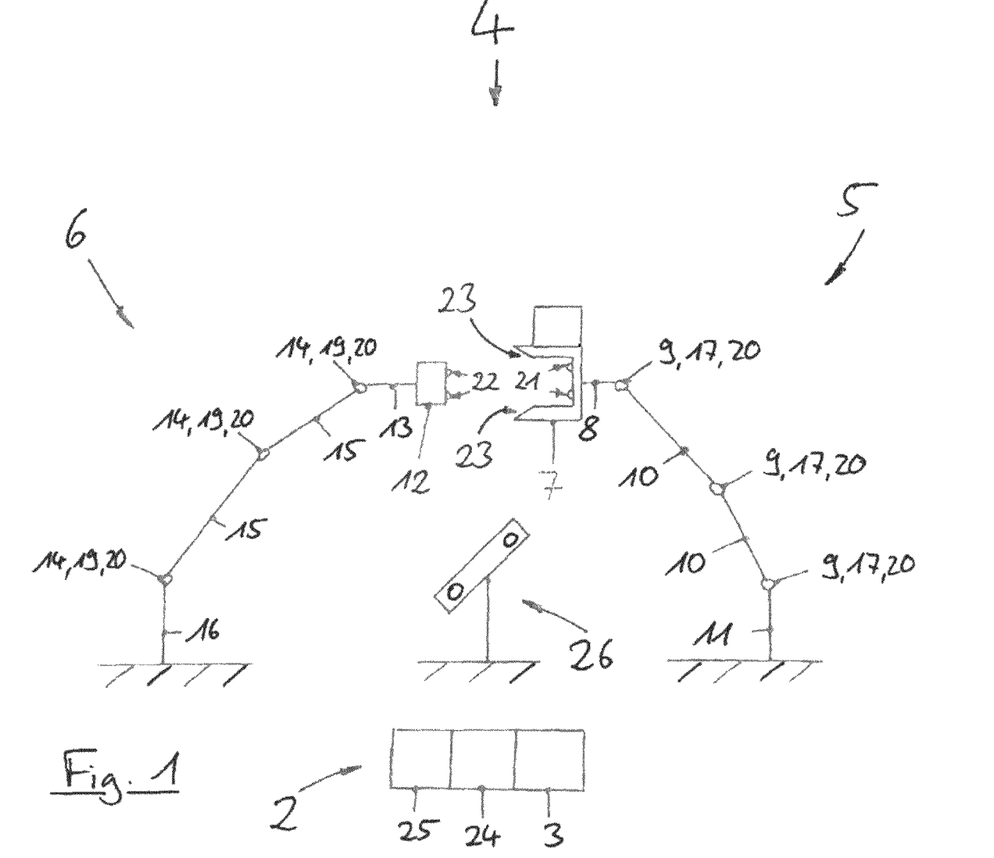
FIG. 1 illustrates a medical carrier system including a motorised and an unmotorised articulated support arm.

FIG. 1 schematically shows a motorised support arm 6 which is adapted to manipulate an unmotorised support arm 5 within a surgical environment. Both support arms 5, 6 comprise a plurality of rigid arm sections 8, 10, 11 and 13, 15, 16, respectively, which are connected to each other via rotatable joints 9 and 14, respectively, each of which provide one single rotatable degree of freedom.

The base sections 11 and 16 of the respective support arms are fixedly mounted to a common base, for example, two opposite mounting rails of a patient couch.

The motorised support arm 6 comprises at its most distal section 13 a mechanical interface 12 along with a control interface 22, which correspond to a mechanical interface 7 and a control interface 21, respectively, provided at the most distal section 8 of the unmotorised support arm(s).

In order to move the predefined section 8 of the unmotorised support arm 5 along with a functional section thereof (schematically shown as square box in FIG. 1) to a desired position, the actuators within or near the joints 14 are controlled by the control unit 25 within the computer 2 to move the mechanical interface 12 into the mechanical interface 7 of the unmotorised support arm 5, such that the control interfaces 21 and 22 connect each other, as well. The mechanical interface 7 features a tapered surface 23 which facilitates the insertion of the mechanical interface 12 into the mechanical interface 7. As soon as interface 12 is fully received by interface 7, an engaging mechanism (not shown in FIG. 1) establishes a force transmitting connection between the interfaces 7 and 12, whereupon only those brakes 17 of the unmotorised support arm 5 are released, which lock the joints 9 that provide the necessary degrees of freedom to move the predefined section 8 to a desired target position. After the predefined section 8 has been moved to its target position by the motorised support arm 6, the brakes 17 are locked again.

In case it is desired to provide a most rigid support for an instrument held via the predefined section 8 (for example the square box thereof in FIG. 1), the interfaces 12 and 7 may remain engaged and the brakes 19 of the motorised support arm 6 may also be locked so as to take up load applied via the predefined section 8 with both of the base sections 11 and 16.

In another case where the motorised support arm 6 needs to perform further tasks, the engagement between the interfaces 12 and 7 as well as the connection between the control interfaces 21 and 22 can be released again such that the most distal section 13 of the motorised support arm 6 can move to a different position as desired.

While performing the above operations, the spatial configuration of support arms 5 and 6 can be sensed via the position sensors/encoders 20 provided in the joints 9 and 14 of both support arms 5 and 6. Additionally or alternatively, an optical tracking system 26 having a stereoscopic camera array can also monitor the spatial position of the mechanical interfaces 7 and 12, for example via tracking markers (not shown in FIG. 1) attached to at least one of the most distal arm sections 8 and 13, particularly to at least one of the mechanical interfaces 7 and 12.

Figure 2:
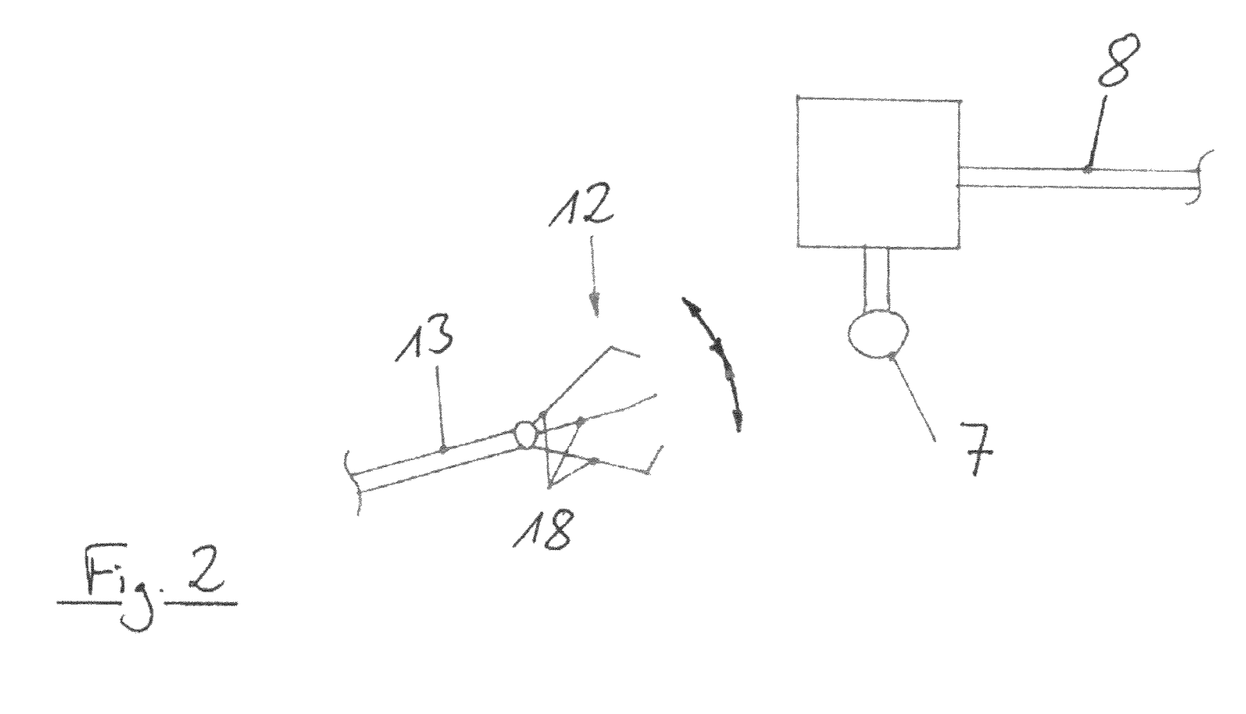
FIG. 2 illustrates an alternative embodiment of mechanical interfaces for the motorised and the unmotorised support arm of FIG. 1.

FIG. 2 shows an alternative embodiment of the mechanical interfaces 7 and 12 at the respective, most distal support arm sections 8 and 13. The mechanical interface 12 of the motorised support arm 6 comprises a gripper 18 as engaging mechanism, comprising a plurality of fingers (three in the shown example) which are adapted to move with respect to each other as shown by arrows in FIG. 2 so to grasp arbitrarily formed objects. As soon as the gripper 12 has been brought into position and the fingers 18 thereof are able to reach around the spherical knob 7 of the unmotorised support arm 5, gripper 12 can firmly grasp knob 7, such that the predefined section 8 can be moved to a desired position by the motorised support arm 6.

Figure 3:
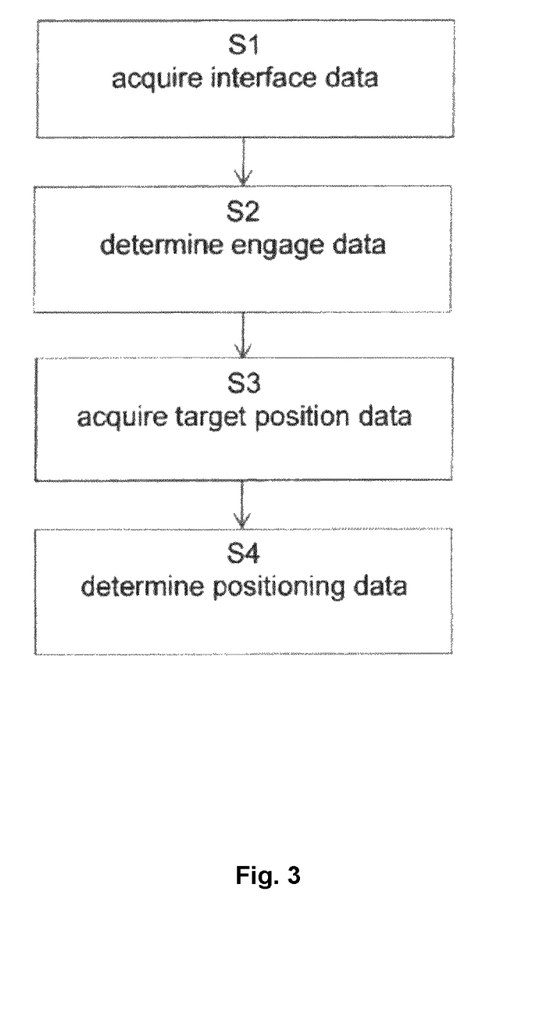
FIG. 3 illustrates the basic steps of the method according to the first aspect.

FIG. 3 shows the basic steps of the method according to the first aspect of the present invention, wherein the specific sequence shown in FIG. 3 is not obligatory. For example, the target position data may be acquired first, whereupon the interface data is acquired to then determine the engage data and the positioning data.

Figure 4:
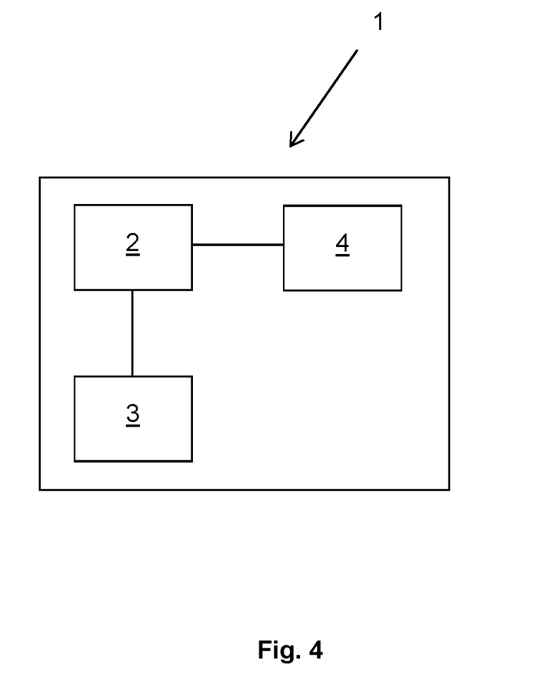
FIG. 4 schematically illustrates the system according to the fifth aspect.

FIG. 4 is a schematic illustration of the medical system 1 according to the fifth aspect. The system is in its entirety identified by reference sign 1 and comprises a computer 2, an electronic data storage device (such as a hard disc) 3 for storing at least the target position data and a medical carrier system 4 according to the first aspect. The components of the medical system 1 have the functionalities and properties explained above with regard to the fifth aspect of this disclosure.

The invention claimed is:

1. A computer-implemented medical method of manipulating at least one first, non-motorized carrier structure via a second, motorized carrier structure, wherein the at least one first carrier structure comprises at least one first adjustable and selectively fixable joint that respectively connects sections of the first carrier structure, and at least one first mechanical interface at a first predefined section of one or more of the sections and/or at one or more of the fixable joints at a first predefined section, and wherein the second carrier structure comprises a second mechanical interface and at least one second adjustable and selectively fixable joint that respectively connects two sections of the second carrier structure, the method comprising:

acquiring interface data at a processor device of a control unit, the interface data describing a spatial position (A) of one or more of a section of the first carrier structure, a joint of the first carrier structure, and the first mechanical interface, to be engaged by the second mechanical interface;

determining by the processor device engage data based on the interface data, wherein the engage data describes control information to cause the second carrier structure to move the second mechanical interface to a spatial position (B) in which the second mechanical interface engages with one or more of the section of the first carrier structure, the joint of the first structure, and the first mechanical interface of the first carrier structure;

acquiring target position data at the processor device, the target position data describing a target position (C) for the first predefined section of the first carrier structure;

determining by the processor device positioning data based on the target position data, wherein the positioning data describes control information to cause the second carrier structure to move the first predefined section to the target position C; and controlling by the processor device and based on the second carrier structure movement of the first predefined section to the target position C.

2. The method according to claim 1, wherein the at least one first joint comprises a controllable first locking mechanism, and wherein:

the determining the engage data comprises determining control information to release the first locking mechanism after the second mechanical interface has engaged with the first carrier structure or before the second carrier structure moves the first predefined section to the target position C; and/or the determining the positioning data comprises determining control information to lock the first locking mechanism after the second carrier structure has moved the first predefined section to the target position C.

3. The method according to claim 1, wherein at least one of the first mechanical interface and the second mechanical interface comprises a controllable engaging mechanism, and wherein:

the determining the engage data comprises determining control information to cause the engaging mechanism to establish a force transmitting connection between the first and the second carrier structure after the second mechanical interface has engaged with the first carrier structure; and/or the determining the positioning data comprises determining control information to cause the engaging mechanism to release the force transmitting connection between the first and the second carrier structure after the first locking mechanism has locked.

4. The method according to claim 1, wherein the at least one second joint comprises a controllable second locking mechanism, and wherein:

the determining the positioning data comprises determining control information to lock the second locking mechanism after the second carrier structure has moved the first predefined section to the target position C and after the first locking mechanism has locked.

5. The method according to claim 1, further comprising:

acquiring secondary target position data that describes a target position (D) for a second predefined section of the second carrier structure; and determining secondary positioning data based on the secondary target position data, wherein the secondary position data describes control information to cause the second carrier structure to move the second predefined section to the secondary target position D.

6. A medical carrier system comprising:

at least one first, non-motorized medical carrier structure comprising at least one first adjustable and selectively fixable joint that respectively connects two sections of the first carrier structure, and at least one first mechanical interface at a first predefined section at one or more of the sections, at one or more of the fixable joints or at a first predefined section; and a second, motorized medical carrier structure comprising a second mechanical interface and at least one second adjustable and selectively fixable joint that respectively connects two sections of the second carrier structure, wherein the second carrier structure is controlled by an associated control unit performing a method to move the second mechanical interface to a spatial position in which the second mechanical interface engages with the first mechanical interface of the non-motorized medical carrier structure, and to move the first predefined section to a target position (C).

7. The system according to claim 6, including one or more of:

the first carrier structure comprises a plurality of first joints, wherein each one of the first joints respectively connects two sections of the first carrier structure;

the second carrier structure comprises a plurality of second joints, wherein each one of the second joints respectively connects two sections of the second carrier structure;

at least one first joint and/or at least one second joint comprises a pivot joint providing a rotational degree of freedom;

at least one first joint and/or at least one second joint comprises a position sensor adapted for determining the relative position of the sections connected via the respective joint;

the first predefined section comprises an end section of the first carrier structure and/or the second predefined section comprises an end section of the second carrier structure;

the first carrier structure comprises a spatially invariant first base section that connects to the first predefined section via the at least one first joint via at least one first intermediate section;

the second carrier structure comprises a spatially invariant second base section which connects to the second predefined section via the at least one second joint via at least one second intermediate section.

8. The system according to claim 6, wherein the first medical carrier structure comprises at least one first control interface and the second medical carrier structure comprises at least one second control interface, wherein at least one first control interface and at least one second control interface are adapted to transmit, particularly via a wireless connection, control information between at least two of:

the first medical carrier structure;

the second medical carrier structure; and a common control unit adapted to control at least one of the first medical carrier structure and the second medical carrier structure, wherein one of the first and the second medical carrier structure is controlled via the control interface of the respective other medical carrier structure.

9. The system according to claim 8, further comprising a first control interface disposed at the first mechanical interface and a second control interface disposed at the second mechanical interface, wherein the first control interface and the second control interface are adapted to transmit control information between the first and the second medical carrier structure when the second mechanical interface engages the first carrier structure.

10. The system according to claim 6, wherein at least one of the first mechanical interface and the second mechanical interface is constituted by a holding or grasping section adapted to hold or grasp a medical instrument or device.

11. The system according to claim 6, wherein at least one of the first mechanical interface and the second mechanical interface comprises at least one of:

a controllable engaging mechanism adapted to establish a releasable positive fit connection between the first mechanical interface and the second mechanical interface; and a magnetic or a physical positioning aid configured to assist in positioning the second mechanical interface at a spatial position (B) in which the second mechanical interface engages with the first mechanical interface.

12. The system according to claim 6, wherein at least one of the first medical carrier structure and the second medical carrier structure is adapted to output a signal indicating whether a force transmitting connection between the first mechanical interface and the second mechanical interface has been established or released.

13. The system according to claim 6, wherein the first mechanical interface and the second mechanical interface are adapted to receive a load that is significantly higher than the load applied to the interfaces by moving the first medical carrier structure via the second medical carrier structure.

14. A non-transient computer readable storage medium storing a computer program comprising instructions that, when executed by a processor of a computer, cause the computer to carry out the method comprising:
  acquiring interface data that describes a spatial position (A) of one or more of a section or of a joint of the first carrier structure, and/or of the first mechanical interface, to be engaged by the second mechanical interface;
  determining engage data based on the interface data, wherein the engage data describes control information to cause the second carrier structure to move the second mechanical interface to a spatial position (B) in which the second mechanical interface engages with one or more of the section or joint and/or the first mechanical interface of the first carrier structure;
  acquiring target position data that describes a target position (C) for the first predefined section of the first carrier structure; and
  determining positioning data is determined based on the target position data, wherein the positioning data describes control information to cause the second carrier structure to move the first predefined section to the target position C.

15. A medical system, comprising:
  a computer comprising a processor;
  at least one electronic data storage device storing target position data; and
  a medical carrier system comprising:
    at least one first, non-motorized medical carrier structure comprising at least one first adjustable and selectively fixable joint that respectively connects two sections of the first carrier structure, and at least one first mechanical interface at a first predefined section of one or more of the sections and/or at one or more of the fixable joints at a first predefined section; and
    a second, motorized medical carrier structure comprising a second mechanical interface and at least one second adjustable and selectively fixable joint that respectively connects two sections of the second carrier structure, wherein the second carrier structure is controlled by an associated control unit performing a method to move the second mechanical interface to a spatial position in which the second mechanical interface engages with the first mechanical interface of the non-motorized medical carrier structure, and to move the first predefined section to a target position (C),
  wherein the at least one computer is operably coupled to the at least one electronic data storage device for acquiring, from the at least one data storage device, at least the target position data, for issuing a control signal to the medical carrier system for controlling the operation of medical carrier system on the basis of the target position data.

16. The system according to claim 6 wherein:
  the second carrier structure is controlled by the associated control unit performing a method of:
    acquiring interface data that describes a spatial position A of one or more of a section of the first carrier structure, a joint of the first carrier structure, and the first mechanical interface, to be engaged by the second mechanical interface;
    determining engage data based on the interface data, wherein the engage data describes control information to cause the second carrier structure to move the second mechanical interface to a spatial position (B) in which the second mechanical interface engages with one or more of the section of the first carrier structure, the joint of the first carrier structure, and the first mechanical interface of the first carrier structure;
    acquiring target position data that describes the target position C for the first predefined section of the first carrier structure; and
    determining positioning data is determined based on the target position data, wherein the positioning data describes control information to cause the second carrier structure to move the first predefined section to the target position C,
  to move the second mechanical interface to the spatial position in which the second mechanical interface engages with the first mechanical interface of the non-motorized medical carrier structure, and to move the first predefined section to the target position C.

* * * * *